United States Patent
Biemans et al.

(10) Patent No.: US 8,084,235 B2
(45) Date of Patent: *Dec. 27, 2011

(54) PURIFICATION PROCESS FOR BACTERIAL CYTOLYSIN

(75) Inventors: Ralph Biemans, Rixensart (BE); Karine Goraj, Rixensart (BE); Emmanuel Mertens, Rixensart (BE); Annick Vandercammen, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 1316 days.

This patent is subject to a terminal disclaimer.

(21) Appl. No.: 10/549,064

(22) PCT Filed: Mar. 11, 2004

(86) PCT No.: PCT/EP2004/002641
§ 371 (c)(1),
(2), (4) Date: Sep. 13, 2005

(87) PCT Pub. No.: WO2004/081515
PCT Pub. Date: Sep. 23, 2004

(65) Prior Publication Data
US 2007/0026010 A1    Feb. 1, 2007

(30) Foreign Application Priority Data

Mar. 13, 2003  (GB) .................................. 0305791.6
Mar. 13, 2003  (GB) .................................. 0305792.4

(51) Int. Cl.
*C12P 21/04* (2006.01)
*A61K 39/02* (2006.01)
*A61K 39/102* (2006.01)

(52) U.S. Cl. ........... 435/71.1; 435/41; 424/9.1; 424/9.2; 424/184.1; 424/234.1; 424/251.1; 424/256.1

(58) Field of Classification Search ................... 424/9.1, 424/9.2, 184.1, 234.1, 251.1, 256.1; 435/41, 435/71.1
See application file for complete search history.

(56) References Cited

U.S. PATENT DOCUMENTS

| 5,258,504 A | 11/1993 | Althaus et al. |
|---|---|---|
| 6,764,686 B2 | 7/2004 | Minetti |

FOREIGN PATENT DOCUMENTS

| EP | 1601689 | 7/2005 |
|---|---|---|
| EP | 1791860 | 6/2007 |
| JP | 10-504717 | 5/1998 |
| WO | WO 90/06951 | 6/1990 |
| WO | WO 96/05859 | 2/1996 |
| WO | WO 96/23061 | 8/1996 |
| WO | WO02/22168 | 3/2002 |
| WO | WO-2004081515 A | 9/2004 |
| WO | WO2006/032499 | 3/2006 |

OTHER PUBLICATIONS

Mitchell et al., "Expression of the Pneumolysin Gene in *Escherichia coli* Rapid Purification and Biological Properties". *Biochim. et Biophys. Acta*, 1007(1): 67-72 (1989).
Queiroz et al., "Hydrophobic Interaction Chromatography of Proteins". *J. Biotechnol.*, 87(2): 143-159 (2001).
Nagamune et al., "Intermedilysin, a Novel Cytotoxin Specific for Human Cells, Secreted by *Streptococcus* Intermedius UNS46 Isolated from a Human Liver Abscess". *Infect. Immun.*, 64(8): 3093-3100 (1996).
Roettger et al., "Adsorption Phenomena in Hydrophobic Interaction Chromatography". *Biotechnol. Progress*, 5(3): 79-88 (1989).
Jiang et al., "Expression and Purification of Src I from Sea Anemone *Sagartia rosea* as a Recombinant Non-fusion Protein". *Protein Expression & Purification*, Academic Press, San Diego, CA, pp. 161-166 (2003).
Johnson M K et al; The Hydrophobic Character of Thiol Activated Cyto Lysins; Biochemical Journal; 1982; 207, No. 3; 557-560.
Paton J et al; Purification and immunogenicity of genetically obtained pneumolysin toxoids and their conjugation to *Streptococcus pneumoniae* type 19F polysaccharide; Infection and Immunity; Jul. 7, 1991; 59, No. 7; 2297-2304.
Gilbert, et al., Two Structural Transitions in Membrane Pore Formation by Pneumolysin, the Pore-Forming Toxin of *S. Pneumoniae*, Cell, 97:647-655 (May 1999).
Gilbert et al., Self-interation of Pneumonlysin, the Pore-Forming Protein toxin of *S. Pneumoniae*, J. Molecular Biology, 284, 1223-1237 (1998).
http://web.archive.org/web/200110423171226/http://www.nestgrp.com/protocols/polylch/hic.shtml (The Nes Group), 2001, accessed Dec. 9, 2009.
Nonfinal rejection dated Jan. 4, 2010, U.S. Appl. No. 11/575,676.
Response to Restriction Requirement, dated Oct. 12, 2009, U.S. Appl. No. 11/575,676.
Restriction Requirement dated Sep. 14, 2009, U.S. Appl. No. 11/575,676.
First Preliminary Amendment, U.S. Appl. No. 11/575,676.
International Preliminary Exam, PCT/EP2005/010258, dated Oct. 12, 2006, 5 pages.
International Search Report, PCT/EP2005/010258, mail date Jan. 30, 2006, 5 pages.
European Patent Office Communication regarding intention to grant application No. 05797390.1 (EP patent 1791860) dated Nov. 12, 2007, 4 pages.
International Search Report, PCT/EP2004/002641 mail date Sep. 3, 2004, 5 pages.

(Continued)

Primary Examiner — Rodney P. Swartz
(74) Attorney, Agent, or Firm — Virginia G. Campen

(57) ABSTRACT

The present invention relates to a method for purifying bacterial cytolysins such as pneumococcal pneumolysin. A single chromatography step produces excellent purification of the cytolysin by binding soluble aggregated cytolysin to a hydrophobic interaction chromatography material in the presence of detergent and high salt.

57 Claims, 5 Drawing Sheets

OTHER PUBLICATIONS

Response to Written Opinion PCT/EP2004/002641, dated Dec. 1, 2004, 7 pages.
Communication from EPO Examining Division application No. 04719447.7 dated Aug. 1, 2006, 3 pages.
International Preliminary Report, PCTEP2004/002641 dated Jun. 10, 2005, 7 pages.
Reply to Communication from Examining Division application No. 04719447.7 dated Oct. 26, 2006, 6 pages.
Reply to Communication from Examining Division application No. 04719447.7, dated Apr. 2, 2007, 5 pages.
Result of Consultation by telephone, application No. 04719447.7, dated Mar. 22, 2007, 1 page.
European Patent Office Communication regarding intention to grant application No. 04719447.7 (EP 1601689), dated Jun. 21, 2007, 4 pages.
Amersham Pharmacia Biotech, Hydrophobic Interaction Chromatography: Principles and Methods, 18-1020-90 Edition AB, Amersham Pharmacia Biotech Inc. , (2000).
Eid and Mogenson, Detergent extraction of the human alpha-beta interferon receptor: a soluble form capable of binding interferon, Biochimica et Biophysica Acta 1034: 114-117 (1990).
Kanclerski and Mollby, Production and Purification of *Streptococcus pneumoniae* Hemolysin (Pneumolysin), J. Clinical Microbiol. 25(2):222-25 (1987).
Kothary and Kreger, Purification and Characterization of an Extracellular Cytolysin Produced by *Vibrio damsela*, Infection and Immunity 49(1):25-31 (1985).
Kothary et al., Purification and Characterization of a Vulnificolysin-Like Cytolysin Produced by *Vibrio tubiashii*. App. Environ. Microbiol. 67(8):3707-11 (2001).
Kothary et al., Purification and Characterization of Enterotoxigenic El Tor-Like Hemolysin Produced by *Vibrio fluvialis*, Infection and Immunity 71(6):3213-20 (2003).
Kuo et al., Characterization of a Recombinant Pneumolysin and Its Use as a protein Carrier for Pneumococcal Type 18C Conjugate Vaccines, Infection and Immunity 63:2706-13 (1995).
Lock et al., Sequence variation in the *Streptococcus pneumoniae* pneumolysin gene affecting haemolytic activity and electrophoretic mobility of the toxin, Microbial Pathogenesis, 21:71-83 (1996).
Miyake et al., Purification and Characterization of *Vibrio metschnikovii* Cytolysin, Infection and Immunity 56(4):954-60 (1988).
Shumway and Klebanoff, Purification of Pneumolysin, Infection and Immunity 4(4):388-92 (1971).
Steinfort et al., Effect of *Streptococcus pneumoniae* on Human Respiratory Epithelium in Vitro, Infection and Immunity 57(7):2006-13 (1989).

Protective effect of GMBS detoxified pneumolysin and PhtD in a mouse challenge model

PURIFICATION PROCESS FOR BACTERIAL CYTOLYSIN

This application is a 371 of International Patent Application No. PCT/EP2004/002641, filed 11 Mar. 2004.

TECHNICAL FIELD

The present invention relates to the field of bacterial cytolysin purification and particularly to a method of purification of pneumolysin. Pneumolysin is a protein from *Streptococcus pneumoniae* with good antigenic properties which is suitable a vaccine component against *S. pneumoniae* infection or otitis media. The method of the invention describes an unusual and advantageous step of purifying pneumolysin in a single chromatographic step by binding it to a hydrophobic interaction column in the presence of detergent and high salt. The process advantageously makes use of the property of bacterial cytolysins of having a high affinity for aromatic compounds resembling cholesterol, particularly when in an aggregated condition and hence will be generally applicable for the purification of members of this family of toxins.

Thiol activated cytolysins form a prominent group of bacterial toxins of which steptolysin O is the prototype (Billington et al FEMS Microbiol. Lett. (2000), 182; 197-205). These toxins are lytic for eukaryotic cells by the formation of pores in the cell membrane. Oxidising agents adversely affect their cytolytic activity whereas reducing agents can restore activity. Members of this group show 30-60% similarity in primary amino acid sequence and contain an almost invariant undecapeptide sequence near the C-terminus. Cholesterol is the major target cell receptor for these toxins. The cytolysins bind to cholesterol containing membranes and oligomerise to form transmembrane pores up to 30 nm in diameter and composed of 40-80 monomer subunits. The binding of membrane cholesterol induces a conformational change in the toxin monomer driving the subsequent events of oligimerisation, membrane insertion and pore formation.

*Streptococcus pneumoniae* is the causative agent of several human diseases including pneumonia, bacteremia, meningitis, otitis media and sinusitis. Sometimes these diseases can lead to fatalities despite the availability of antibiotics. The emergence of antibiotic resistant strains of *S. pneumoniae* has aggravated the problems caused by this pathogen. In this context, it is important for effective vaccines against *S. pneumoniae* to be developed.

Polyvalent pneumococcal vaccines containing purified capsular polysaccharides have been available for several years. Their application is limited by poor immunogenicity particularly in high-risk groups including infants, the elderly and those with sickle-cell anaemia, multiple myeloma, cirrhosis or alcoholism. They also provide serotype specific protection and only 23 out of 90 known serotypes are covered by existing formulations. This will give protection against 90% of serotypes found in the US population but against only approximately 70% of serotypes found in Asian populations. Recently a conjugated seven-valent vaccine has become available, which similarly has problems protecting against all pneumococcal strains.

Pneumolysin (Ply) is a 53 kDa thiol-activated cytolysin found in all strains of *S. pneumoniae*, which is released on autolysis and contributes to the pathogenesis of *S. pneumoniae*. It is highly conserved with only a few amino acid substitutions occurring between the Ply proteins of different serotypes. Pneumolysin's high degree of conservation and its immunogenicity make it a potential candidate as a vaccine component. However, wild-type Ply is unsuitable for incorporation into vaccines for use in humans because of its toxicity. Ply causes damage to cell membranes by interacting with membrane-bound cholesterol and oligomerising to form pores in the membrane. A conserved cysteine-containing motif found near the C-terminus has been implicated in the lytic activity. Mutations of Ply have been suggested to lower this toxicity (WO90/06951, WO99/03884).

A two step method for the purification of pneumolysin has been described by Lock et al (Microbial Pathogenesis (1996) 21; 71-83). Recombinant pneumolysin is purified from an *E. coli* culture using a combination of ion-exchange and gel filtration chromatography. The method involves the steps of preparing an extract and passing it down a DEAE-Sepharose column followed by a Sephacryl S200-HR column. This method could be used to purify recombinant or native pneumolysin.

Kuo et al describe a method of purifying recombinant GST-pneumolysin fusion protein (Infection and Immunity (1995) 63; 2706-2713). The fusion protein is expressed in an *E. coli* culture and a cell lysate is loaded onto a glutathione agarose gel. The fusion protein is eluted with glutathione and thrombin can be used to cleave the fusion protein. The proteins were passed over a glutathione-agarose column again to remove GST. The affinity purified pneumolysin was further purified using a hydroxylapatite column.

Mitchell et al (BBA (1989) 1007; 67-72) describe a method of purifying pneumolysin using hydrophobic interaction chromatography. Under the conditions that they use (250 mM salt), the pneumolysin failed to bind tightly to the column although its progress was retarded and the pneumolysin eluted as a broad peak. Additional steps of determining which fractions contained pure pneumolysin, concentrating the positive fractions, reloading onto the column and eluting with a small volume of water were needed to overcome the problem of the pneumolysin not binding tightly to the column material.

There remains a continuing need for improved vaccines against *S. pneumoniae*. The incorporation of a Ply component has promise although the toxicity of the protein remains a problem. The development of a rapid and effective procedure for the bulk purification of pneumolysin is also required. Methods described previously involve the use of multiple purification steps with intervening assay and concentration steps. The present invention provides a more efficient purification method which advantageously uses a single chromatography step, which is capable of being used to purify large batches of pneumolysin.

Panel A shows the gel after coomassie blue staining. Panel B shows the gel after a Western blotting procedure using anti-*E. coli* antibodies to probe for contaminating proteins.

Figure 2:
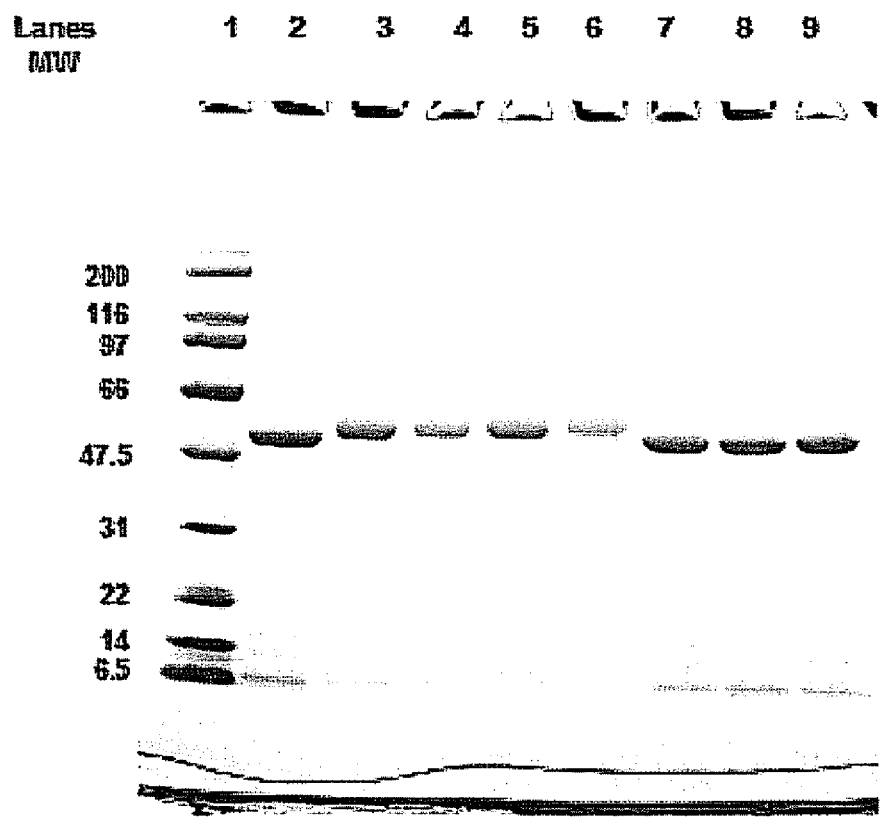

FIG. 2—SDS-PAGE analysis of GMBS (N-(γ-maleimidobutyryloxy)succinimide ester) modified pneumolysin-coomassie blue stained.

The following samples were run on an SDS-PAGE gel:— lane 1—molecular weight standards, lane 2—unmodified pneumolysin, lane 3—PLY treated with GMBS at a molar ratio of GMBS/lysine of 4/1, lane 4—PLY treated with GMBS at a molar ratio of GMBS/lysine of 4/1 and incubated for 7 days at 37° C., lane 5—PLY treated with GMBS at a molar ratio of GMBS/lysine of 8/1, lane 6—PLY treated with GMBS at a molar ratio of GMBS/lysine of 8/1 after incubation for 7 days at 37° C., lane 7—PLY treated with Sulfo-NHS acetate at a molar ratio of NHS/lysine of 10/1, lane 8—PLY treated with NEM, lane 9—PLY treated with NEM after 7 days incubation at 37° C.

Figure 3:
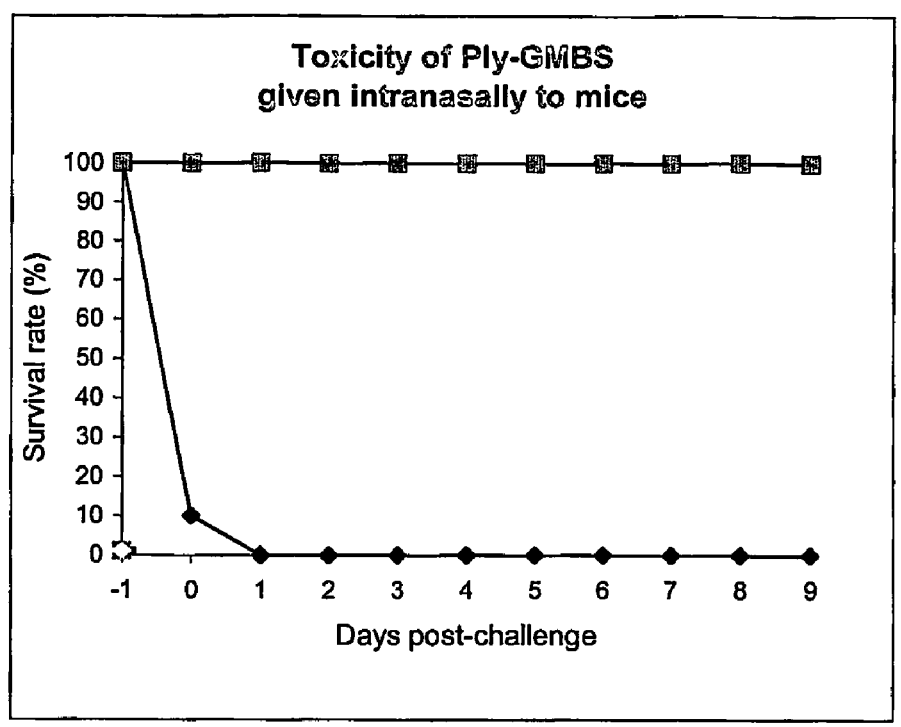

FIG. 3—Toxicity of GMBS treated pneumolysin given intranasally to mice. The line marked with diamonds indicates survival rate for mice challenged with 2 ug native pneumolysin. The line marked with squares indicates the survival rate for mice challenged with 10 ug GMBS treated pneumolysin.

Figure 4:
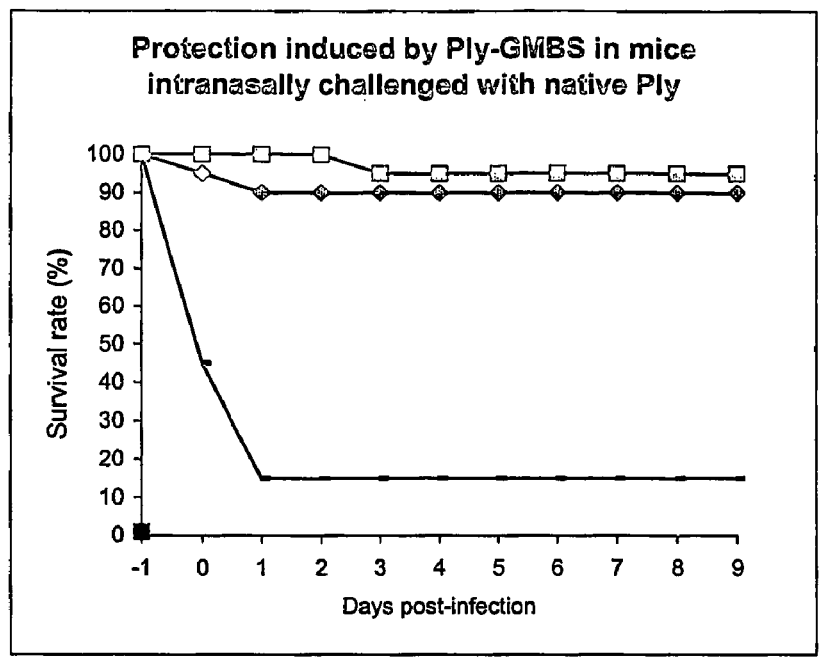

FIG. 4—Protection induced by GMBS treated pneumolysin in mice challenged intranasally with native pneumolysin. The line marked with rectangles shows survival rate in mice inoculated with adjuvant alone. The line marked with diamonds indicates the survival rate for mice inoculated with native pneumolysin. The line marked with squares indicates the survival rate for mice inoculated with GMBS treated pneumolysin.

FIG. 5—Protection induced by inoculation with PhtD and GMBS treated pneumolysin in mice challenged intranasally with type 2 D39 pneumococcal strain. The line marked with rectangles represents survival rate for mice inoculated with adjuvant alone. The line marked with diamonds represents the survival rate for mice inoculated with PhtD. The line marked with squares represents the survival rate for mice inoculated with PhtD and GMBS treated pneumolysin.

DETAILED DESCRIPTION

Processes

The process of the invention is a method for purifying a bacterial cytolysin such as pneumolysin. A cytolysin, for instance pneumolysin, is purified using only a single column chromatography step without requiring reloading onto the column. The protein is bound in an aggregated form to a hydrophobic interaction column in the presence of detergent and salt. Few proteins bind to the column under these conditions allowing purification of a cytolysin in a single step.

For the purposes of the invention a soluble aggregate of a cytolysin, preferably pneumolysin is an aggregated form of the cytolysin that remains in the supernatant after centrifugation at 30,000 g for 20 minutes. The soluble aggregate is retained on hydrophobic interaction chromatography material, preferably phenyl-Sepharose, in the presence of high salt, preferably 1M. Optionally, the soluble aggregate is colloidal.

The cytolysin, preferably pneumolysin is bound to the column as a soluble aggregate. It is unusual to load aggregates onto a column for various reasons including filters or columns clogging and loss of material. However, by using a detergent that reduces the size of the aggregates to form a soluble aggregate, it is found that these aggregates bind tightly to the column under detergent conditions but may be eluted at a purity of at least 50%, 60%, 70%, 80%, preferably 90%, 95%, more preferably 97%, 98% or 99% as assessed by SDS-PAGE analysis without adversely affecting the column filters. The process preferably gives a yield of at least 100, 200, 500, 700, more preferably 1000, 1500, 1700 or 1900 mg of cytolysin, preferably pneumolysin per litre of fermentation. Preferably at least 1%, 2%, 5%, 7%, 9% or 10% of the protein from the fermentation culture is recovered as purified cytolysin, preferably pneumolysin.

The process exploits the ability of cytolysins such as pneumolysin to bind to cholesterol and other aromatic compounds. This binding is particularly tight when the cytolysin is aggregated, allowing the cytolysin to bind in the presence of detergent. The process can be extended to other members of the cytolysin family since all members share the ability to bind to aromatic compounds and form pores. In fact the method could be used to purify other families of protein that bind to cholesterol or other aromatic compounds and/or form pores, preferably both.

Accordingly, in a first embodiment, a process for bacterial cytolysin purification is provided comprising the steps of:
 a) growing a culture of cells expressing bacterial cytolysin;
 b) preparing an extract from the culture containing bacterial cytolysin;
 c) binding soluble aggregated bacterial cytolysin contained in the extract in the presence of detergent (preferably aliphatic detergent) to a hydrophobic interaction chromatography material under high salt (preferably 0.5-2M salt) conditions;
 d) eluting bacterial cytolysin in the presence of detergent (preferably aliphatic detergent) under low salt (preferably 0-0.2M salt) conditions.

In a second embodiment a process for bacterial cytolysin purification is provided comprising the steps of:
 a) growing a culture of cells expressing bacterial cytolysin;
 b) preparing an extract from the culture containing bacterial cytolysin;
 c) binding bacterial cytolysin contained in the extract to hydrophobic interaction chromatography material in the presence of a solution containing 0.5-2M salt and 0.1%-5% detergent;
 d) eluting bacterial cytolysin using a low salt (preferably 0-0.2M salt) solution containing 0.1-5% detergent.

In either of the above embodiments, the process of the invention preferably comprises the further steps of:
 e) removing detergent from the bacterial cytolysin
 f) solubilising the bacterial cytolysin by addition of a denaturant;
 g) removing the denaturant from the bacterial cytolysin.

The process of the invention can be advantageously used to purify pneumococcal pneumolysin. Other cytolysins that can be purified by the method of the invention include pyolysin from *A. pyogenes*, cereolysin from *B. cereus*, thuringiolysin O from *B. thuringiensis*, laterosporolysin from *B. latersporus*, bifermentolysin from *C. bifermentans*, botukinolysin from *C. botulinum*, chauveolysin from *C. chauvoel*, histolyticolysin from *C. histolyticum*, oedematolysin from *C. novyi* type A, perfringolysin O from *C. perfringens*, septicolysin O from *C. septicum*, sordellilysin from *C. sordellii*, tetanolysin from *C. tetani*, ivanolysin O from *L. ivanovi*, listeriolysin O from *L. monocytogenes*, seeligerilysin O from *L. seellgeri*, alveolysin from *P. alvei*, streptolysin O from *S. pyogenes*, *S. canis* or *S. equisimilis*, intermedilysin from *S. intermedius*, suilysin from *S. suis* or pneumolysin from *S. pneumoniae* which may be of wild type or may be a genetically modified toxins with lower levels of toxicity such as PdA and PdB described above.

By pneumolysin or Ply it is meant: native pneumolysin from pneumococcus or recombinant pneumolysin, wild-type pneumolysin or mutants of pneumolysin (e.g. those described in WO90/06951 and WO99/03884). Optionally, pneumolysin can also mean any fragment of pneumolysin or any variant of pneumolysin which shares at least 70, 80, 90 or 95% amino acid sequence identity with a wild-type pneumolysin sequence, which still retains the ability to be purified by the methods of the invention, as easily determined by a skilled person.

In preferred embodiments of the invention, the same detergent is present in steps b) and c), b) and d), c) and d), more preferably in steps b), c) and d), preferably at a concentration of 0.1%-5% (w/v). For the purposes of the invention, an aliphatic detergent is defined as a substantially aliphatic detergent with insufficient aromatic character to prevent binding of cytolysin to the column in step c). Preferably, the detergent will have one or less aromatic rings, most preferably it has no aromatic rings. During step b), it is advantageous for the detergent to break up larger aggregates of cytolysin into smaller aggregates which make a soluble aggregate. During steps c) and d), the detergent advantageously retains the soluble aggregated state of the cytolysin, allowing it to bind to the column in high salt conditions with high affinity.

The cytolysin, preferably pneumolysin is expressed in a culture of bacterial cells, preferably S. pneumoniae, E. coli or alternatively in yeast cells, insect cells, mammalian cells or any other expression system suitable for its expression. In expression systems that produce high yields of pneumolysin, the pneumolysin often becomes aggregated of its own accord and the process of the invention is ideal for its purification. Preferably pneumolysin is expressed at high yields so that it makes up more than 2, 3, 4, 5, 7 or 10% of total protein in the expression system. Preferably the pneumolysin is in aggregated form and hence mostly devoid of haemolytic activity. For example, expression in E. coli in a fermentor under a phage λ promoter or other promoters that allow high expression are well known to the person skilled in the art.

Preferably, the cytolysin is extracted from the expression system as an aggregate. Alternatively, a lower yield expression system may provide soluble cytolysin. In this case, the extract containing cytolysin, preferably pneumolysin is adjusted to a pH below 7.5 which allows the cytolysin to aggregate over a period of at least 8 hours, preferably at least 24 hours.

The preparation of an extract in step b) preferably involves one or more steps of mechanically breaking the cells and/or treating the cells with detergent. If made with a high yield method, the pneumolysin remains in the form of aggregates but the aggregates should be small enough so that they remain in the supernatant after centrifugation of the sample under conditions necessary for pelleting insoluble cellular debris. Preferably the detergent used in the invention is an aliphatic detergent which does not contain aromatic rings, preferably an ionic detergent, more preferably a cationic or anionic detergent and most preferably, the detergent is sodium lauroyl sarcosinate. Preferred detergents are able to solubilise pneumolysin whilst leaving it in the form of small aggregates that bind to the hydrophobic interaction column without causing blockage of filters attached to the column. Preferred detergents are able to reduce the size of pneumolysin aggregates, allowing the pneumolysin aggregates to be sufficiently small so that they remain in the supernatant after centrifugation of the sample at 30,000 g for 20 minutes. Such soluble aggregates are purifiable as such on the hydrophobic interaction column. The detergent is present at a concentration of between 0.1% and 5%, preferably 0.5% and 3% (w/v), preferably between 0.75% and 2%, more preferably around 1%. Preferably, the detergent is dialysable.

Following mechanical and/or detergent disruption of the culture in step b), the process of the invention includes centrifugation of the cell material and collecting the supernatant as the extract to be loaded onto the chromatography material during step c). Pneumolysin is preferably present in the supernatant as a soluble aggregate.

The process of the invention uses hydrophobic interaction chromatography to purify pneumolysin in a single step. The column material used in step c) preferably contains aromatic groups, preferably phenyl groups and more preferably is phenyl-sepharose.

The solution used in step c) and/or step d) during loading and elution of the column comprises an ionic detergent, preferably a cationic or anionic detergent, preferably a detergent which is soluble at salt concentrations above 0.5M, most preferably the detergent is sodium lauroyl sarcosinate. The detergent used is one which will reduce the size of cytolysin, preferably pneumolysin, aggregates, allowing the cytolysin to be present in the sample as a soluble aggregate so that it will bind to the hydrophobic interaction column material without being irreversibly stuck on the column. The detergent is present at a concentration of preferably between 0.1% and 5%, preferably 0.5% and 3% (w/v), more preferably between 0.75% and 2%, most preferably around 1%.

The solution used in step c) and/or d) contains a salt, preferably a salt selected from the group consisting of sodium chloride, magnesium chloride, ammonium chloride, sodium sulphate, magnesium sulphate, ammonium sulphate, sodium phosphate, magnesium phosphate, ammonium phosphate and is preferably buffered at pH 6-8, preferably around pH 7. Any buffer capable of maintaining the pH between pH 5 and 9 may be used.

The solution used to bind pneumolysin to the column in the process of the invention contains a high salt concentration, preferably 0.6-2M, more preferably around 1M. The salt concentration is chosen such that pneumolysin is in a soluble aggregated form and is capable of binding to the hydrophobic chromatography material.

Optionally, step c) can contain an extra step of washing the column in intermediate salt conditions of around 0.5M salt or a salt concentration capable of removing any poorly binding impurities.

The process of the invention uses a decreasing salt gradient to elute pneumolysin from the column. Preferably the low salt solution used to make the salt gradient in step d) contains between 0-0.1M salt, more preferably 0-40 mM salt. Alternatively, step wise elution may be used with the low salt buffer used in step d) containing between 0-0.2M salt, more preferably 0-40 mM salt.

Optional steps may be added to the process of the invention if it is preferred to denature the pneumolysin and subsequently refold it by removal of the denaturant. These optional steps ensure that pure cytolysin, preferably pneumolysin, with a native structure is obtained. The first optional step e) involves the removal of detergent by diafiltration, dialysis or dilution. This step preferably involves diafiltration/dialysis against a buffer of pH 8-10, preferably around 9, more preferably the buffer is one able to buffer at alkaline pH values, most preferably the buffer is DEA. The solution is preferably of low ionic strength, preferably 10-50 mM, most preferably around 25 mM. Diafiltration or dialysis is preferably carried out at 4° C. but is alternatively carried out at room temperature.

In a second optional step, cytolysin, preferably pneumolysin is denatured and solubilised by addition of a denaturant. Preferably the denaturant used in step f) is guanidine hydrochloride, more preferably 5-8M guanidine hydrochloride, most preferably around 6M guanidine hydrochloride. The pneumolysin is incubated with guanidine hydrochloride for at least 10 minutes, preferably for at least 1 hour, more preferably for about one hour.

The cytolysin, preferably pneumolysin is preferably then contacted with 5-9M urea, preferably around 8M urea during step f). This is achieved by diafiltration or dialysis of the cytolysin, preferably pneumolysin against urea. Preferably, the same buffer and pH are maintained during the exchange of denaturant. Preferably, a reducing agent (DTT, 2-mercaptoethanol or glutathione is added during the exchange of denaturant.

Preferably step f) involves contacting cytolysin, preferably pneumolysin with 5-8M guanidine hydrochloride followed by exchanging the guanidine hydrochloride for 5-9M urea.

In order to prevent inappropriate disulphide bonds forming while the cytolysin, preferably pneumolysin is denatured, it is advantageous to ensure that a reducing agent is present during at least part of steps f) and g). A preferred reducing agent is 0.1-10 mM DTT, preferably around 1 mM DTT. Alternatively glutathione or 2-mercaptoethanol is used. Preferred concentration of glutathione are 1-50 mM, more preferably 10-30 mM.

Optional step g) involves removal of the denaturant in order to refold cytolysin, preferably pneumolysin, preferably by diafiltration or dialysis against a low salt buffer of pH 6-11, preferably around pH 9. Preferably cytolysin, preferably pneumolysin concentration is maintained at at least 100 ug/ml, preferably between 100 ug/ml and 1000 ug/ml, more preferably at around 500 ug/ml. Optionally, diafiltration or dialysis is against a buffer containing propylene glycol at between 10 and 30%, preferably at around 15%. Preferably a reducing agent as described above is maintained during step g). Diafiltration or dialysis is preferably carried out at 4° C. but is alternatively carried out at room temperature.

A further optional step h) involves the removal of the reducing agent after cytolysin, preferably pneumolysin has refolded. This is preferably achieved by diafiltration or dialysis against a low salt buffer of pH 6-11, preferably around pH 9. Optionally, diafiltration or dialysis is against a buffer containing propylene glycol at between 10 and 30%, preferably at around 15%. Diafiltration or dialysis is preferably carried out at 4° C. but is alternatively carried out at room temperature.

In preferred methods of the invention, the cytolysin, preferably pneumolysin is refolded so that its haemolytic activity is restored to above 25%, 50%, 75% most preferably to above 90% of that of the properly folded protein. For the purposes of the invention, 'folded' protein is a protein having the tertiary structure of the protein made by a non-denaturing process. In the case of wild type pneumolysin, the expected haemolytic activity of refolded pneumolysin would be 500,000-1,000,000 haemolytic units/mg pneumolysin. In the case of point mutated pneumolysin with a lower haemolytic activity, the haemolytic activity of the refolded pneumolysin would be correspondingly lower.

Detoxification of a Toxin

The cytolysin purified by the method of the invention, preferably pneumolysin may be subjected to a further optional step of detoxification by chemical treatment. This additional step is particularly advantageous if the cytolysin, preferably pneumolysin is to be administered to an animal or a human. Wild type pneumolysin is highly toxic. Several mutated pneumolysin proteins have been isolated that have reduced toxicity, yet these still retain residual toxicity that may be problematic when the pneumolysin is administered internally (WO99/03884, WO90/06951). Alternatively it can be detoxified by conjugation to polysaccharides (WO96/05859).

The process of the invention may detoxify either wild type or mutated cytolysin, for example pneumolysin by chemical treatment. Preferred embodiments use a crosslinking agent, more preferably containing one or more chemicals selected from the group consisting of formaldehyde, glutaraldehyde and a cross-linking reagent containing an N-hydroxysuccinomido ester and/or a maleimide group (e.g. GMBS).

The detoxification processes themselves are an aspect of the invention and can be used to detoxify bacterial toxins, preferably pneumolysin prepared by other methods.

In one embodiment, the detoxification method of the invention describes the detoxification of a bacterial toxin comprising treating the toxin with a chemical compound, preferably a crosslinking reagent that is reactive, preferably preferentially reactive, most preferably specifically reactive with amine groups, more preferably primary amine groups.

For the purposes of this application, a cross linking reagent is defined as a compound with at least two reactive groups, at least one of which is capable of reacting with at least one group on the bacterial toxin. A further reactive group is able to react with either a group on the bacterial toxin or a separate compound (for instance an amino acid, peptide, polypeptide, sugar or polysaccharide).

Preferably, the chemical compound or the crosslinking reagent is reactive, more preferably preferentially reactive, most preferably specifically reactive with amine and sulfhydryl groups. Preferably, the chemical compound reacts with a primary amine group of lysine, more preferably, the crosslinking reagent reacts with a primary amine group of lysine and the sulfhydryl group of cysteine. This method is particularly advantageous where pneumolysin is detoxified since modification of both cysteine and lysine residues leads to a synergistic decrease in the level of hemolysis compared to the residual hemolysis activity where the cross-linking reagent reacts with only lysine or cysteine.

Thus an alternative embodiment provides a method of detoxifying bacterial toxins comprising modifying a cysteine residue (optionally near the C-terminus of the toxin) involved in the toxic activity of the toxin (preferably the lytic activity) comprising treating the toxin with a cross-linking reagent (preferably a heterobifunctional cross-linking reagent) that cross-links the sulfhydryl groups with another amino acid of the toxin, preferably more than 2, 5, 10, 15, 20, 30, 40 amino acids away from the cysteine in the primary structure. Preferably the other amino acid contains a primary amine group and more preferably the amino acid is lysine.

In some embodiments, over 50%, 60%, 70%, 80%, 90% or 95% of the toxin retains a molecular weight within 5%, 10%, 20%, 30%, 40%, 50%, 60%, 70%, 80% or 90%, more preferably between 1-50%, most preferably between 5-10% of its original molecular weight after the treatment as assessed by SDS-PAGE. Preferably the toxin acquires a slightly higher molecular weight following the detoxification treatment due to several amino acid residues becoming modified by covalently binding to the chemical compound. However the method of the invention preferably does not involve extensive conjugation of the toxin, either by covalently binding it to other toxin molecules so that a toxin with a multimeric quaternary structure is formed, or by covalently binding the toxin to other large proteins, polysaccharides or lipopolysaccharides. Most preferably the methods, proteins or products disclosed in WO96/05859 are not covered by this invention.

The methods of the invention may be used to detoxify bacterial toxins. Preferred toxins include the thiol-activated cytolysins pyolysin from *A. pyogenes*, cereolysin from *B. cereus*, thuringiolysin O from *B. thuringiensis*, laterosporolysin from *B. latersporus*, bifermentolysin from *C. bifermentans*, botukinolysin from *C. botulinum*, chauveolysin from *C. chauvoel*, histolyticolysin from *C. histolyticum*, oedematolysin from *C. novyi* type A, perfringolysin O from *C. perfringens*, septicolysin O from *C. septicum*, sordellilysin from *C. sordellii*, tetanolysin from *C. tetani*, ivanolysin O from *L. ivanovi*, listeriolysin O from *L. monocytogenes*, seeligerilysin O from *L. seeligeri*, alveolysin from *P. alvei*, streptolysin O from *S. pyogenes, S. canis* or *S. equisimilis*, intermedilysin from *S. intermedius*, suilysin from *S. suis* or pneumolysin from *S. pneumoniae* which may be of wild type or may be a genetically modified toxins with lower levels of toxicity such as PdA and PdB described above (WO90/06951, WO99/03884).

The method may also be used to detoxify the Neisserial toxins FrpA, FrpC (WO92/01460), FrpB (Microbiology 142; 3269-3274, (1996); J. Bacteriol. 181; 2895-2901 (1999)) NM-ADPRT (13$^{th}$ International Pathogenic *Neisseria* Conference 2002 Masignani et al p135). FrpA and FrpC contain a region which is conserved between these two proteins and a preferred fragment of the toxins would be a polypeptide containing this conserved fragment, preferably comprising amino acids 227-1004 of the sequence of FrpA/C.

The method of the invention may also be used to detoxify Bordetella toxins including adenylate cyclase (CyaA) (Glaser (1988) Mol. Microbiol. 2; 19-30), dermonecrotic toxin (Livey (1984) J. Med, Microbiol. 17; 91-103) and pertussis toxin (PT) (Munoz et al (1981) Infect Immun 33; 820-826). The method of the invention is also useful for detoxifying tetanus toxin (TT) and diphtheria toxin (DT) and toxin from *S. aureus* and *S. epidermidis* including autolysin and haemolysin (WO01/98499, WO02/59148).

Methods of the invention lead to a reduction of the amount of toxicity and/or haemolytic activity of the toxin of at least 90%, preferably 95%, 96%, 98%, 99%, 99.5%, 99.9% or 99.99%. (Haemolytic activity is measured using the method of Example 3 and toxicity may be measured by the method of Example 5.) Native pneumolysin has a haemolytic activity of 500,000-1,000,000 units per mg of pneumolysin. Some point-mutated variants of pneumolysin have reduced toxicity and haemolytic activity. Detoxification of a variant pneumolysin may not be able to achieve as large a percentage decrease in haemolytic activity due to the lower starting point form which haemolytic activity is reduced, however it is envisioned that the majority of the remaining haemolytic activity is removed by the methods of the invention.

The detoxification step of the method of the invention preferably provides a cross-linking reaction which is substantially non-reversible. Reversibility is assessed by monitoring the level of haemolytic activity of the detoxified toxin directly after detoxification and after incubating at a temperature above 25° C., preferably above 30° C., more preferably above 35° C., most preferably above 37° C. for at least 5, 6, 7, 8, 9 or 10 days. A substantially non-reversible reaction results in substantially non-reversible detoxification and is defined as a reaction where the level of haemolytic activity rises by less than 100%, 50%, 40%, 30%, 20% 10% after incubation at an elevated temperature as described above. Many methods of detoxification, for instance by using formaldehyde treatment, result in detoxification that is not stable but increases in toxicity over time.

In a preferred detoxification step of the method of the invention over 50%, 60%, 70%, 80%, 90%, 95%, or 98% of the toxin retains a monomeric quaternary structure after the cross-linking reaction. Many cross-linking reagents form intermolecular crosslinks (for example formaldehyde and glutaraldehyde). This can effect the immunological properties of the toxin since some epitopes will be hidden within the aggregate. Methods of the invention preferably involve simply modifying amino acid residues, preferably sulfhydryl and/or primary amine groups of amino acids and/or the formation of mainly intramolecular crosslinks. The resultant monomeric quaternary structure allows epitopes to remain exposed on the surface of the toxin.

In a preferred embodiment of the detoxification step, the cross-linking reagent is heterobifunctional. Preferred crosslinking reagents contain an N-hydroxysuccinimide ester group that reacts preferentially, more preferably specifically, with primary amine groups. Preferably the cross-linking reagent contains a maleimide group that reacts preferentially, more preferably specifically, with sulfhydryl groups. At a pH around 7, a maleimide group reacts 1000 fold faster with sulfhydryl groups than it does with amines. Preferably, the cross-linking reagent contains both an N-hydroxysuccinimide ester group and a maleimide group. The crosslinking agent is preferably not cleavable using a reducing agent since this leads to less effective detoxification.

The distance between the reactive groups of the cross-linking reagent is able to effect the efficiency of detoxification. Preferably, the distance between the groups of the crosslinking reagent that are reactive with amine and sulfhydryl groups is between 1.5 and 20 Angstroms, more preferably between 5 and 15 Angstroms and most preferably around 10 Angstroms in the method of the invention. Preferably, amino acid residues on the bacterial toxin are modified by addition of a group that is over 5, 7, 10, 12, 15, 18, 20, 50, 100, 500 Angstroms long. Preferably, the modifying group is between 5 and 100 Angstroms, more preferably between 10 and 20 Angstroms in size.

The detoxification step of the method of the invention allows sufficient residues to be modified so that steric interference and/or conformational changes inhibit the function of the bacterial toxin. Preferably at least 5, 7, 10, 12, 14, 15, 20 or 25 amino acid residues of the bacterial toxin are modified. Where unreacted maleimide groups are present on the cross-linking reagent, an Ellman reaction can be used to estimate (indirectly) the number of crosslinker molecules attached to each molecule of toxin (Ellman 1959 Arch. Biochem. Biophys. 82; 70).

Preferred crosslinking reagents are SMPT, Sulfo-LC-SMPT, Sulfo-KMUS, LC-SMCC, KMUA, Sulfo-LC-SPDP, LC-SPDP, SMPB, Sulfo-SMPB, SMPH, Sulfo-SMCC, SMCC, SIAB, Sulfo-SIAB, GMBS (N-(γ-maleimidobutyryloxy)succinimide ester), Sulfo-GMBS, MBS, Sulfo-MBS, Sulfo-EMCS, EMCA, EMCS, BMPS, SPDP, SBAP, BMPA, AMAS, SATP and SIA (Pierce).

In a preferred method of the invention the toxin is treated with the chemical compound or crosslinking reagent under pH conditions of between 5.0 and 9.0, preferably 6.5 to 8.0, most preferably 7.0 to 7.8. In treatments where the reaction of a maleimide group to a sulfhydryl group is encouraged, the preferred pH of the reaction is 6.0 and 8.0, more preferably 6.5 and 7.5. The preferred concentration of salts during the reaction is between 100 mM and 1M, more preferably 150 mM and 500 mM, most preferably between 200 mM and 300 mM. However, the inventors have found that it is sometimes preferable to perform the reaction at low salt concentration where no sodium chloride or other salt is added. Where the reaction is performed at a pH of between 7.6 and 7.8, the reaction can optionally be carried out without the addition of salt. Similarly, the use of higher ratios of GMBS to toxin can be performed without the addition of salt at pH values between 7.0 and 8.0.

Preferably a 50-500, more preferably 130-350 or 350-900, most preferably around 250 fold molar excess of the chemical compound or crosslinking reagent to each toxin is used. Pneumococcal pneumolysin contains 31 lysine residues. Therefore a 248 fold molar excess of chemical compound or cross-linking reagent over pneumolysin is equivalent to an 8 fold molar excess of chemical compound or cross-linking reagent to each lysine residue. Preferably a 2-20, more preferably a 4-15 or 15-30, most preferably around 8 fold molar ratio of chemical compound or cross-linking reagent to lysine residues is used in methods of the invention.

The treatment with crosslinking reagent proceeds for at least 15 minutes, preferably for at least 30 minutes, most preferably for around one hour at between 4° C. and 40° C., preferably between 15° C. and 25° C., most preferably at room temperature. The method of the invention may further comprise a quenching step using a compound containing a sulfhydryl group, preferably the quenching compound has a molecular weight of over 50, 100 or 120, more preferably the quenching reagent is an amino acid such as cysteine. Alternatively the groups may be reacted with a peptide or polysaccharide moiety capable of reacting with maleimide, for instance a peptide containing a cysteine residue. This is particularly appropriate where unreacted maleimide group are present prior to the quenching step.

The detoxification step is suitable for use on bacterial toxins as described above. Preferably the bacterial toxin is from *Streptococcus pneumoniae*, most preferably the toxin is pneumolysin. The pneumolysin is a native or recombinant protein or a protein that has been genetically engineered to reduce its toxicity (as described above). Fusion proteins of toxins, preferably pneumolysin or fragments of toxins, preferably pneumolysin may be detoxified using the method of the invention.

Thus in a preferred embodiment, a toxin (such as pneumolysin) is detoxified with a cross-linking reagent which is preferably heterobifunctional having groups that are reactive with lysine and cysteine residues and is of a certain size, most preferably having the reactive groups spaced 10-20 Angstroms apart such that either or preferably both or the following occurs:

a) between 5 and 30, preferably around 12-14 amino acid residues of the toxin are modified by a cross-linker molecule covalently binding preferably to a lysine or arginine residue (preferably, as measured indirectly by an Ellman reaction), the other end having been quenched (preferably with cysteine) and/or;

b) a cysteine sidechain involved in the toxic activity of the toxin (preferably towards the C-terminus of the toxin) is cross-linked to another sidechain of the toxin (preferably to a lysine or arginine residue) which is preferably separated by more than 2, 5, 10, 20, 30 or 40 amino acids from the cysteine residue in the primary sequence of the toxin.

In a further preferred embodiment, a toxin (preferably pneumolysin) is detoxified with a monofunctional chemical compound which preferably reacts with amino acids containing a primary amine group, more preferably lysine, and is of a certain size, most preferably 10-100 Angstroms such that the toxin is covered with between 5 and 30, more preferably around 14 chemical compound bound to amino acid residues.

Polysaccharide Conjugates

A problem associated with the polysaccharide approach to vaccination, is the fact that polysaccharides per se are poor immunogens. To overcome this, polysaccharides may be conjugated to protein carriers, which provide bystander T-cell help. The process of the invention may advantageously contain a further step of conjugating the cytolysin, preferably pneumolysin to a bacterial polysaccharide, for instance a lipo-oligosaccharide or preferably a capsular polysaccharide.

A preferred conjugate of the invention comprises cytolysin, preferably pneumolysin obtained by the method of the invention conjugated to capsular polysaccharides derived from *Streptococcus pneumoniae*. The pneumococcal capsular polysaccharide antigens are preferably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most preferably from serotypes 1, 3, 4, 5, 6B, 7F, 9V, 14, 18C, 19F and 23F), or mixtures of two or more of said conjugates (4, 7, 9, 11, 13 or 23).

Cytolysin, preferably pneumolysin, purified by the process of the invention is also preferably conjugated to capsular polysaccharides from other strains of bacteria. Such polysaccharides can be isolated from, for example, *H. influenzae*, *H. influenzae* type B (Hib) *N. meningitidis* groups A, C, W, Y, Streptococci other than *S. pneumoniae* (e.g., Group B *Streptococcus*, *S. pyogenes*, etc.), *Staphylococcus* (e.g., *S. aureus*, *S. epidermidis*), *E. coli*, *Enterococcus* (e.g., *E. faecalis* and *E. faecium*), etc. Preferably the polysaccharides are from *H. influenzae* type B (Hib), and/or *N. meningitidis* groups A, C, W135, and/or Y.

The polysaccharide may be linked to cytolysin, preferably pneumolysin, by any known method (for example, by Likhite, U.S. Pat. No. 4,372,945 and by Armor et al., U.S. Pat. No. 4,474,757). Preferably, CDAP conjugation is carried out (WO 95/08348). To enhance immunogenicity, the polysaccharides may be adjuvanted and/or lyophilised. The polysaccharides of the invention may be full size or sized post purification to smaller polysaccharides or oligosaccharides.

The process of the invention preferably comprises a further step of formulating cytolysin, preferably pneumolysin into a vaccine.

Proteins and Immunogenic Compositions

A further embodiment of the invention is cytolysin, preferably pneumolysin, purified by the method of the invention. This includes a pneumolysin-bacterial capsular polysaccharide conjugate made by the process of the invention.

A further embodiment of the invention is an immunogenic composition comprising cytolysin, preferably pneumolysin or pneumolysin-bacterial capsular polysaccharide obtained by the process of the invention (as described above).

The immunogenic composition of the invention preferably further comprises one or more members of the pneumococcal choline binding protein family, preferably choline binding protein A or an immunogenic fragment thereof and/or one or more members of the poly histidine triad family (including fusion proteins thereof, preferably PhtA, PhtB, PhtD or PhtE or an immunogenic fragment thereof.

Concerning the Choline Binding Protein family (CbpX), members of this family were originally identified as pneumococcal proteins that could be purified by choline-affinity chromatography. All of the choline-binding proteins are non-covalently bound to phosphorylcholine moieties of cell wall teichoic acid and membrane-associated lipoteichoic acid. Structurally, they have several regions in common over the entire family, although the exact nature of the proteins (amino acid sequence, length, etc.) can vary. In general, choline binding proteins comprise an N terminal region (N), conserved repeat regions (R1 and/or R2), a proline rich region (P) and a conserved choline binding region (C), made up of multiple repeats, that comprises approximately one half of the protein. As used in this application, the term "Choline Binding Protein family (CbpX)" is selected from the group consisting of Choline Binding Proteins as identified in WO97/41151, PbcA, SpsA, PspC, CbpA, CbpD, and CbpG. CbpA is disclosed in WO97/41151. CbpD and CbpG are disclosed in WO00/29434. PspC is disclosed in WO97/09994. PbcA is disclosed in WO98/21337. SpsA is a Choline binding protein disclosed in WO 98/39450. Preferably the Choline Binding Proteins are selected from the group consisting of CbpA, PbcA, SpsA and PspC.

Another preferred embodiment is CbpX truncates wherein "CbpX" is defined above and "truncates" refers to CbpX proteins lacking 50% or more of the Choline binding region (C). Preferably such proteins lack the entire choline binding region. More preferably, the such protein truncates lack (i) the choline binding region and (ii) a portion of the N-terminal half of the protein as well, yet retain at least one repeat region (R1 or R2). More preferably still, the truncate has 2 repeat regions (R1 and R2), more preferably the truncate retains the proline rich region (P). Examples of such preferred embodiments are NR1xR2 and R1xR2 as illustrated in WO99/51266 or WO99/51188 and NR1XR2P, however, other choline binding proteins lacking a similar choline binding region are also contemplated within the scope of this invention.

The LytX family is membrane associated proteins associated with cell lysis. The N-terminal domain comprises choline binding domain(s), however the LytX family does not have all the features found in the CbpA family noted above and thus the LytX family is considered distinct from the CbpX family. In contrast with the CbpX family, the C-terminal domain contains the catalytic domain of the LytX protein family. The family comprises LytA, B and C. With regards to the LytX family, LytA is disclosed in Ronda et al., Eur J Biochem, 164:621-624 (1987). LytB is disclosed in WO 98/18930, and is also referred to as Sp46. LytC is also disclosed in WO 98/18930, and is also referred to as Sp91. A preferred member of that family is LytC.

Another preferred embodiment are LytX truncates wherein "LytX" is defined above and "truncates" refers to LytX proteins lacking 50% or more of the Choline binding region. Preferably such proteins lack the entire choline binding region. An example of such truncates can be found in the Examples section of this invention.

Yet another preferred embodiment of this invention are CbpX truncate-LytX truncate chimeric proteins (or fusions). Preferably this comprises NR1xR2 (or R1xR2, or NR1XR2P) of CbpX and the C-terminal portion (Cterm, i.e., lacking the choline binding domains) of LytX (e.g., LytC-Cterm or Sp91 Cterm). More preferably CbpX is selected from the group consisting of CbpA, PbcA, SpsA and PspC. More preferably still, it is CbpA. Preferably, LytX is LytC (also referred to as Sp91).

Another embodiment of the present invention is a PspA or PsaA, or truncates lacking the choline binding domain (C) optionally expressed as a fusion protein with LytX. Preferably, LytX is LytC.

The Pht (Poly Histidine Triad) family comprises proteins PhtA, PhtB, PhtD, and PhtE. The family is characterised by a lipidation sequence, two domains separated by a proline-rich region and several histidine triads, possibly involved in metal or nucleoside binding or enzymatic activity, (3-5) coiled-coil regions, a conserved N-terminus and a heterogeneous C terminus. It is present in all strains of pneumococci tested. Homologous proteins have also been found in other Streptococci and Neisseria. Preferred members of the family comprise PhtA, PhtB and PhtD. More preferably, it comprises PhtA or PhtD. It is understood, however, that the terms PhtA, B, D, and E refer to proteins having sequences disclosed in the citations below as well as naturally-occurring (and man-made) variants thereof that have a sequence homology that is at least 90% identical to the referenced proteins. Preferably it is at least 95% identical and most preferably it is 97% identical.

The imunogeni composition of the invention may incorporate fusion proteins of histidine triad proteins. Preferred fusion proteins contain i) PhtD or a fragment thereof linked to PhtE or a fragment thereof or ii) PhtB or a fragment thereof linked to PhtE or a fragment thereof.

With regards to the PhtX proteins, PhtA is disclosed in WO 98/18930, and is also referred to Sp36. As noted above, it is a protein from the polyhistidine triad family and has the type II signal motif of LXXC.

PhtD is disclosed in WO 00/37105, and is also referred to Sp036D. As noted above, it also is a protein from the polyhistidine triad family and has the type II LXXC signal motif. PhtB is disclosed in WO 00/37105, and is also referred to Sp036B. Another member of the PhtB family is the C3-Degrading Polypeptide, as disclosed in WO 00/17370. This protein also is from the polyhistidine triad family and has the type II LXXC signal motif. A preferred immunologically functional equivalent is the protein Sp42 disclosed in WO 98/18930. A PhtB truncate (approximately 79 kD) is disclosed in WO99/15675 which is also considered a member of the PhtX family.

PhtE is disclosed in WO00/30299 and is referred to as BVH-3.

In order to generate an immunogenic composition of the invention, capable of eliciting an immune response against more than one pathogen involved in otitis media, it is advantageous for immunogenic compositions of the invention to further comprise an antigen from one or more (2, 3, 4, 5, 6) of S. pneumoniae, non-typable Haemophilus influenzae, Moraxella catarrhalis, RSV, parainfluenza virus and/or influenza virus.

The present invention also contemplates combination vaccines which provide protection against a range of different pathogens. Many paediatric vaccines are now given as a combination vaccine so as to reduce the number of injections a child has to receive. Thus for paediatric vaccines other antigens from other pathogens may be formulated with the vaccines of the invention. For example the vaccines of the invention can be formulated with (or administered separately but at the same time) the well known 'trivalent' combination vaccine comprising Diphtheria toxoid (DT), tetanus toxoid (TT), and pertussis components [typically detoxified Pertussis toxoid (PT) and filamentous haemagglutinin (FHA) with optional pertactin (PRN) and/or agglutinin 1+2], for example the marketed vaccine INFANRIX-DTPa™ (SmithKlineBeecham Biologicals) which contains DT, TT, PT, FHA and PRN antigens, or with a whole cell pertussis component for example as marketed by SmithKlineBeecham Biologicals s.a., as Tritanrix™. The combined vaccine may also comprise other antigen, such as Hepatitis B surface antigen (HBsAg), Polio virus antigens (for instance inactivated trivalent polio virus—IPV), Moraxella catarrhalis outer membrane proteins, non-typeable Haemophilus influenzae proteins, N. meningitidis B outer membrane proteins.

Examples of preferred Moraxella catarrhalis protein antigens which can be included in a combination vaccine (especially for the prevention of otitis media) are: OMP106 [WO 97/41731 (Antex) & WO 96/34960 (PMC)]; OMP21; LbpA &/or LbpB [WO 98/55606 (PMC)]; TbpA &/or TbpB [WO 97/13785 & WO 97/32980 (PMC)]; CopB [Helminen M E, et al. (1993) Infect. Immun. 61:2003-2010]; UspA1 and/or UspA2 [WO 93/03761 (University of Texas)]; OmpCD;

HasR (PCT/EP99/03824); PilQ (PCT/EP99/03823); OMP85 (PCT/EP00/01468); lipo06 (GB 9917977.2); lipo10 (GB 9918208.1); lipo11 (GB 9918302.2); lipo18 (GB 9918038.2); P6 (PCT/EP99/03038); D15 (PCT/EP99/03822); OmplA1 (PCT/EP99/06781); Hly3 (PCT/EP99/03257); and OmpE. Examples of non-typeable *Haemophilus influenzae* antigens which can be included in a combination vaccine (especially for the prevention of otitis media) include: Fimbrin protein [(U.S. Pat. No. 5,766,608—Ohio State Research Foundation)] and fusions comprising peptides therefrom [eg LB1(f) peptide fusions; U.S. Pat. No. 5,843,464 (OSU) or WO 99/64067]; OMP26 [WO 97/01638 (Cortecs)]; P6 [EP 281673 (State University of New York)]; TbpA and/or TbpB; Hia; Hsf; Hin47; Hif; Hmw1; Hmw2; Hmw3; Hmw4; Hap; D15 (WO 94/12641); protein D (EP 594610); P2; and P5 (WO 94/26304).

Other combinations contemplated are the cytolysin, preferably pneumolysin of the invention in combination with viral antigens, for example, from influenza (attenuated, split, or subunit [e.g., surface glycoproteins neuraminidase (NA) and haemagglutinin (HA). See, e.g., Chaloupka I. et al, Eur. Journal Clin. Microbiol. Infect. Dis. 1996, 15:121-127], RSV (e.g., F and G antigens or F/G fusions, see, eg, Schmidt A. C. et al, J Virol, May 2001, p4594-4603), parainfluenxa virus 3 (PIV3) (e.g., HN and F proteins, see Schmidt et al. supra), *Varicella* (e.g., attenuated, glycoproteins I-V, etc.), and any (or all) component(s) of MMR (measles, mumps, rubella).

Vaccines

A further embodiment of the invention is a vaccine comprising cytolysin, preferably pneumolysin or a pneumolysin-bacterial capsular polysaccharide conjugate, obtained by the process of the invention and a pharmaceutically acceptable excipient and optionally an adjuvant.

A vaccine of the invention may comprise the immunogenic compositions of the invention described above and a pharmaceutically acceptable excipient.

Vaccines of the invention are capable of generating a protective immune response against *S. pneumoniae* infection and/or otitis media.

A further embodiment of the invention includes a method of making a vaccine by taking a cytolysin, preferably pneumolysin, made by the process of the invention and formulating it as a vaccine with a pharmaceutically acceptable excipient and optionally with one or more of the further antigens described above.

A further embodiment of the invention includes method of treatment or prevention of bacterial infection, preferably *Streptococcus pneumoniae* infection or otitis media comprising administration of the vaccine or immunogenic composition of the invention.

A further embodiment of the invention is the use of the cytolysin, preferably pneumolysin and/or pneumolysin—bacterial capsular polysaccharide conjugate, either of which is obtained by a process of the invention, in the preparation of a vaccine for the treatment or prevention of bacterial infection, preferably *Streptococcus pneumoniae* infection or otitis media.

The vaccines of the present invention are preferably adjuvanted. Suitable adjuvants include an aluminium salt such as aluminium hydroxide gel (alum) or aluminium phosphate, but may also be a salt of calcium, magnesium, iron or zinc, or may be an insoluble suspension of acylated tyrosine, or acylated sugars, cationically or anionically derivatised polysaccharides, or polyphosphazenes.

It is preferred that the adjuvant be selected to be a preferential inducer of a TH1 type of response. Such high levels of Th1-type cytokines tend to favour the induction of cell mediated immune responses to a given antigen, whilst high levels of Th2-type cytokines tend to favour the induction of humoral immune responses to the antigen.

It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p145-173). Traditionally, Th1-type responses are associated with the production of the INFγ and IL-2 cytokines by T-lymphocytes. Other cytokines often directly associated with the induction of Th1-type immune responses are not produced by T-cells, such as IL-12. In contrast, Th2-type responses are associated with the secretion of II-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminium salt (for instance aluminium phosphate or aluminium hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1].

An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739.

A particularly potent adjuvant formulation involving QS21, 3D-MPL and tocopherol in an oil in water emulsion is described in WO 95/17210, and is a preferred formulation.

Preferably the vaccine additionally comprises a saponin, more preferably QS21. The formulation may also comprise an oil in water emulsion and tocopherol (WO 95/17210).

The present invention also provides a method for producing a vaccine formulation comprising mixing a cytolysin of the present invention together with a pharmaceutically acceptable excipient, such as 3D-MPL.

Unmethylated CpG containing oligonucleotides (WO 96/02555) are also preferential inducers of a TH1 response and are suitable for use in the present invention.

In a further aspect of the present invention there is provided a vaccine as herein described for use in medicine. In one embodiment there is a method of preventing or ameliorating pneumonia in an elderly human (over 55 years old) comprising administering a safe and effective amount of a vaccine of the invention, and optionally a Th1 adjuvant, to said elderly patient.

In a further embodiment there is provided a method of preventing or ameliorating otitis media in Infants (up to 24 months) or toddlers (typically 24 months to 5 years), comprising administering a safe and effective amount of a vaccine comprising a cytolysin, preferably pneumolysin of the invention, optionally with one or more of the further antigens described above and optionally a Th1 adjuvant, to said Infant or toddler.

The vaccine preparations of the present invention may be used to protect or treat a mammal (preferably a human patient) susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance if polysaccharides are present in a vaccine these could be administered separately at the same time or 1-2 weeks after the administration of the bacterial protein combination for optimal coordination of the immune responses with respect to each other). In addition to a single route of administration, 2 different routes of administration may be used. For example, viral antigens may be administered ID (intradermal), whilst bacterial proteins may be administered IM (intramuscular) or IN (intranasal). If polysaccharides are present, they may be administered IM (or ID) and bacterial proteins may be administered IN (or ID). In addition, the vaccines of the invention may be administered IM for priming doses and IN for booster doses.

The amount of conjugate antigen in each vaccine dose is selected as an amount which induces an immunoprotective response without significant, adverse side effects in typical vaccines. Such amount will vary depending upon which specific immunogen is employed and how it is presented. The content of protein antigens in the vaccine will typically be in the range 1-100 μg, preferably 5-50 μg, most typically in the range 5-25 μg. If polysaccharides are included, generally it is expected that each dose will comprise 0.1-100 μg of polysaccharide, preferably 0.1-50 μg, more preferably 0.1-10 μg, of which 1 to 5 μg is the most preferable range.

Optimal amounts of components for a particular vaccine can be ascertained by standard studies involving observation of appropriate immune responses in subjects. Following an initial vaccination, subjects may receive one or several booster immunisations adequately spaced. Typically a vaccine will comprise antigen (proteins), an adjuvant, and excipients or a pharmaceutically acceptable carrier.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

Although the vaccines of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms a preferred feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

When the vaccines of the present invention are to be administered to the skin, or more specifically into the dermis, the vaccine is in a low liquid volume, particularly a volume of between about 0.05 ml and 0.2 ml.

The content of antigens in the skin or intradermal vaccines of the present invention may be similar to conventional doses as found in intramuscular vaccines. Accordingly, the protein antigens present in the intradermal vaccines may in the range 1-100 μg, preferably 5-50 μg. Likewise, if present, the amount of polysaccharide conjugate antigen in each vaccine dose is generally expected to comprise 0.1-100 μg of polysaccharide, preferably 0.1-50 μg, preferably 0.1-10 μg, and may be between 1 and 5 μg. However, it is a feature of skin or intradermal vaccines that the formulations may be "low dose". Accordingly the protein antigens in "low dose" vaccines are preferably present in as little as 0.1 to 10 μg, preferably 0.1 to 5 μg per dose; and if present the polysaccharide conjugate antigens may be present in the range of 0.01-1 μg, and preferably between 0.01 to 0.5 μg of polysaccharide per dose.

As used herein, the term "intradermal delivery" means delivery of the vaccine to the region of the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

The immunogenic compositions and vaccines of the invention can be evaluated in various animal models or with human sera. As an illustration, the following animal models can be used to evaluate pneumococcal infection. C3H/HeJ Mice (6 to 8 week old) can be immunised s.c. with 15 μg protein adjuvanted with 50 μl CFA, followed 3-4 weeks later by boosting with 15 μg protein with IFA. For demonstrating passive and active protection from systemic infection, mice can be administered intraperitoneally with immune sera or proteins prior to challenge by intraperitoneal injection with 15 to 90 LD50 pneumococci on week 8-10. Additionally, proteins can be tested in a mouse nasopharynx colonization model by (Wu et al Microbial Pathogenesis 1997; 23:127-137).

In addition to mice, infant rats are susceptible to colonisation and infection by S. pneumoniae. In passive protective studies, administration of mouse immune sera (100 ul i.p. or 10 ul i.n.) can be done prior to challenge with intranasal administration of S. pneumonia (10 ul) in 2-5 day old infant rat pups. Colonisation can be determined by plating nasal washes (20-40 ul instilled, 10 ul withdrawn).

Favourable interactions between the protein (or protein and polysaccharide) components of the combination vaccine may be demonstrated by administering a dose of each protein (or protein and polysaccharide) in the vaccine which would be sub-protective in a monovalent vaccine. Increased protective efficacy of the combination vaccine compared to monovalent vaccines can be attributed to a favourable interaction between the components.

The invention is illustrated in the accompanying examples. The examples are carried out using standard techniques, which are well known and routine to those of skill in the art, except where otherwise described in detail. The examples are meant to illustrate, but not limit the invention.

EXAMPLES

Example 1

Purification of Pneumolysin

After 18 hours induction of the E. coli culture by increasing the temperature to 39.5.degree. C., the E. coli were pelletted by centrifugation at 17,000 g for 1 hour. The pellet was resuspended in 25 mM diethanolamine pH9.0 and the E. coli were mechanically broken using one pass at 500 PSI in a Rannie apparatus. 1% Sodium lauroyl sarcosinate (SLS) was added to the broken E. coli and the mixture was incubated for 1 hour at room temperature before centrifugation at 30,000 g for 20 minutes so that cellular debris was pelleted. The supernatant was diluted 2.5 fold to end up in 20 mM phosphate pH 7.0 containing 1M NaCl and 1% SLS and was then loaded onto a phenyl-sepharose HP column equilibrated in the same buffer (20 mM phosphate pH 7.0 containing 1M NaCl and 1% SLS=equilibration buffer). The column was washed with 4 column volumes of equilibration buffer followed by 2 column volumes of 20 mM phosphate buffer pH7.0 containing 0.5M NaCl and 1% SLS. Pneumolysin was eluted from the column by applying a low salt buffer containing 20 mM phosphate buffer pH 7.0 containing 1% SLS. Fractions containing pneumolysin were identified using SDS-PAGE analysis, were pooled and the buffer was exchanged to 25 mM diethanolamine pH 9.0 using diafiltration.

The pneumolysin was solubilised by denaturation by adding solid guanidine hydrochloride up to 6M final concentration and incubating for one hour. It was then diafiltered against 8M urea in 25 mM diethanolamine pH9.0 containing 1 mM DTT. Pneumolysin was refolded by diafiltration against 20 mM borate buffer pH9.0 containing 1 mM DTT. After renaturation, DTT was removed by diafiltration against 20 mM borate buffer pH 9.0.

The purity of the pneumolysin achieved was analysed by running on an SDS-PAGE and staining with Coomassie brilliant blue. A separate gel was analysed by Western blotting using an antibody against E. coli to detect the level of E. coli proteins remaining in the purified pneumolysin preparation. The biological activity of the purified pneumolysin was assessed using an in vitro haemolysis assay.

Results

Figure 1:
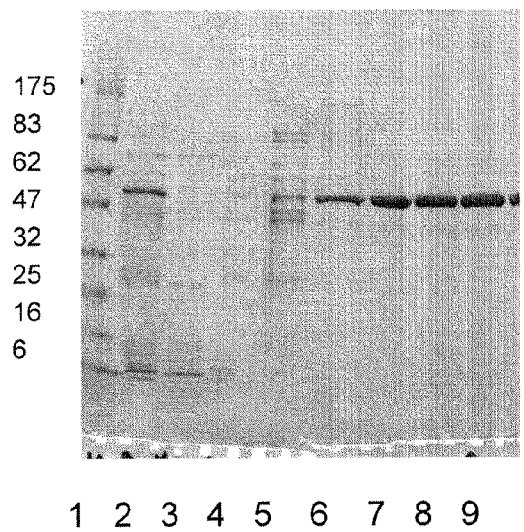
FIG. 1—SDS-PAGE gels showing the purification of pneumolysin. The following samples were run on SDS-PAGE gels:—lane 1—molecular weight standards, lane 2—supernatant of cell extract, lane 3—phenyl-sepharose flow through, lane 4 phenyl sepharose first wash, lane 5—phenyl-sepharose second wash, lane 6 phenyl-sepharose wash with 0.5M NaCl, lane 7 Phenyl-sepharose elution with low salt buffer, lane 8 pneumolysin after denaturation/refolding steps, lane 9—pneumolysin after sterilizing filtration.
Figure 1:
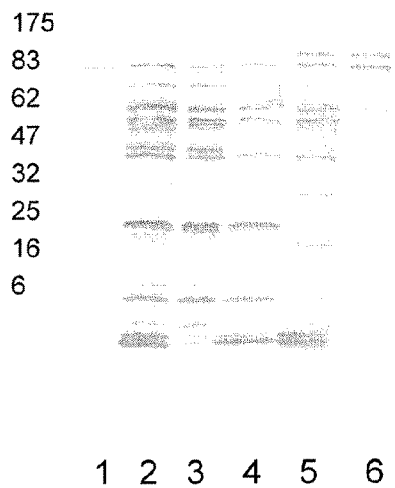

As shown in FIG. 1, the method described above was able to produce a highly efficient purification of pneumolysin after a single chromatography step. The Coomassie blue stained gel in panel A shows that elution of the column with a low salt buffer containing no added sodium chloride was able to elute a 53 kDa band corresponding to pneumolysin from the column in a highly purified form. The much fainter band of approximately 45 kDa is also thought to be pneumolysin since this second band binds to anti-pneumolysin antibodies (results not show) and also fails to bind to the anti E. coli antibodies as shown in panel B. The Western blot of panel B is a highly sensitive method of detecting any contaminating proteins that remain in the purified pneumolysin. This method was able to detect very few contaminants and those present were at a low level that was below the detection level of Coomassie staining. The pneumolysin is therefore purified to a level of 98-100% purity.

The yield of the purification method is also good with a typical run giving around 1900 mg of pneumolysin per litre of fermentation. Approximately 10% of the protein from the fermentation culture was recovered as purified pneumolysin.

The activity of the pneumolysin in a haemolysis assay was assessed after the pneumolysin had been treated with guanidinium hydrochoride/urea and had been refolded by removal of the denaturant. Haemolytic activity was detected in dilutions of the purified pneumolysin down to concentrations of 1.3 ng/ml showing that haemolytic activity had been re-established. This corresponds to between 500,000 and 1,000,000 Haemolytic units per mg of wild-type pneumolysin.

Example 2

Detoxification of S. pneumoniae Pneumolysin Using GMBS

Purified pneumolysin was detoxified by modification of sulfhydryl and primary amine groups using the NHS ester-maleimide crosslinking reagent GMBS (N-(γ-maleimidobutyryloxy)succinimide ester). Pneumolysin at a concentration of 0.5 mg/ml, was dialysed against 50 mM phosphate buffer pH 7.0. The GMBS was initially dissolved in DMSO and was added to pneumolysin in at a 248-fold molar excess of GMBS. Treatment continued for one hour at room temperature. Excess GMBS and by-products were removed by dialysis against 100 mM sodium phosphate pH 6.8. Further maleimide groups were quenched by reacting with 0.6 mg/ml cysteine for two hours at room temperature. In order to remove excess cysteine, the sample was dialysed against 2 mM sodium phosphate pH7.15.

Example 3

Characterization of Detoxified Pneumolysin

Haemolytic Activity

A hemolytic assay was used to assess the remaining toxicity of detoxified pneumolysin. Serial 2-fold dilutions of pneumolysin were incubated with sheep red blood cells. After centrifugation, the supernatant was transferred to immunoplates and released haemoglobin was measured using optical density reading at 405 nm. Results were expressed as ng/ml pneumolysin corresponding to the mid-point of the OD curve.

The assay was repeated after incubating the detoxified pneumolysin at 37° C. for 7 days to monitor the reversibility of detoxification.

As shown in Table 1, treatment with GMBS was able to substantially reduce the haemolytic activity of PLY with up to a 3,000 fold reduction in haemolytic activity being achieved. Higher molar ratios of GMBS/lysine were able to produce better removal of haemolytic activity with ratios of 4/1 and 5/1 being optimal in this experiment. This treatment was estimated to result in modification of about 14 lysine residues. Where fewer lysine residues were modified, the reduction in haemolytic activity was less.

Elisa

The antigenicity of the detoxified pneumolysin was assessed by ELISA. The ELISA plates were coated with a guinea pig anti-pneumolysin antibody. Samples containing dilutions of pneumolysin were incubated in the plates for 1 hour at room temperature. After washing, the bound pneumolysin was detected using rabbit polyclonal antibodies against pneumolysin, conjugated to horseradish peroxidase. After washing the plates, a substrate reaction was used to assess the amount of pneumolysin bound to each well.

As shown in Table 1, treatment with GMBS led to some loss of antigenicity as assessed by ELISA. However ELISA readings of approximately 66% of that given by untreated PLY could be achieved showing that many antibodies could still recognize the modified pneumolysin.

SDS-PAGE-Analysis

The detoxified pneumolysin proteins were run on an SDS-PAGE (Novex 4-20% polyacrylamide gel Invitrogen) and Coomassie brilliant blue was used to visualize the proteins. As shown on FIG. 2, treatment with GMBS led to a slight increase in the molecular weight of PLY from 53 kDa to approximately 56 kDa. This increase is due to the modification of multiple amino acid residues with GMBS. A small percentage of PLY is converted to multimeric forms as seen by the appearance of faint bands of molecular weight of approximately 110 kDa and 170 kDa, however, most of the PLY remains in an essentially monomeric form. Incubation of the PLY at 37° C. for 7 days did not results in any substantial change in the appearance of the PLY on an SDS-PAGE showing that the modified PLY is not subject to degradation or subsequent covalently-linked multimer formation.

TABLE 1

Trials of PLY detoxification by GMBS

| Trial | GMBS excess (GMBS/Lysine) | Maleimide functions | Ratio ELISA/LOWRY | | Hemolytic titer ng/ml | |
|---|---|---|---|---|---|---|
| | | | 4° C. | 7D37° C. | 4° C. | 7D37° C. |
| | | | % | | | |
| 1 | / | / | 95 | 56 | 1.7 | 4.2 |
| | 1/1 | 8 | 63 | 87 | 186 | 111 |
| | 1.5/1 | 8.5 | 69 | / | 48 | / |
| | 2/1 | 9.4 | 76 | / | 309 | / |
| | 3/1 | 11.8 | 56 | / | 530 | / |
| | 4/1 | 13.5 | 66 | / | 6308 | / |
| | 5/1 | 14.2 | 67 | / | 4284 | / |
| 2 | 4/1 | 13.8 | 26.2 | 24.8 | NH | NH |
| | 8/1 | 17.6 | 23.9 | 38.0 | NH | NH |
| 3 | 4/1 | 11.3 | 89 | 46 | 1598 | 6309 |

Trials were realised on 1 mg of PLY (1 mg/ml) except for the last assay for which 3 mg were treated (PLY at 0.68 mg/ml).

Example 4

Reactogenicity Evaluation of Detoxified Pneumolysin in Rats

Groups of three OFA rats were immunised once by intramuscular (tibialis) inoculation with saline, the adjuvant QS21 (U.S. Pat. No. 5,057,540), pneumolysin, adjuvanted pneumolysin, formaldehyde deto)(ified pneumolysin, adjuvanted formaldehyde detoxified pneumolysin, GMBS detoxified pneumolysin, adjuvanted GMBS detoxified pneumolysin, NHS-acetate detoxified pneumolysin or adjuvanted NHS-acetate detoxified pneumolysin. Three days after immunisation, all the rats were killed and the tibialis were prepared for histological examination. The tibialis were fixed in formalin and cut into 2 mm slices which were dehydrated and paraffin embedded. 7 um sections were cut and stained using the Trichrome Masson method, before being examined microscopically.

Reactogenicity was evaluated using four criteria; degeneration/necrosis, endomysial inflammation, haemorrhage and aponeurosis inflammation. For each histological criterion, a score was attributed to each muscle of each group and a mean lesion score was then calculation for each group. A score of 0=normal, 1=minimal, 2=slight, 3=moderate, 4=marked and 5=severe.

Results

The histology of sections was examined. The mean scores for degeneration/necrosis, endomysial inflammation, haemorrhage and aponeurosis inflammation are shown in Table 2.

TABLE 2

| Inoculation | Degeneration/ Necrosis | Endomysial inflammation | Haemorrhage | Aponeurosis inflammation |
|---|---|---|---|---|
| NaCl | 0 | 0.5 | 0 | 0 |
| Ply | 3.6 | 3.8 | 3.0 | 1.4 |
| GMBS-Ply | 0.6 | 1.3 | 1.3 | 0.4 |
| Adjuvant | 2.9 | 3.9 | 2.8 | 2.8 |
| Ply + adjuvant | 4.2 | 3.9 | 4.6 | 1.8 |
| GMBS-Ply + adj | 2.9 | 3.9 | 3.8 | 1.6 |

A comparison of histological scores for unadjuvanted native and detoxified pneumolysin shows that GMBS is a particularly effective cross-linking reagent to use for the detoxification of pneumolysin, producing a large decrease in degeneration/necrosis, endomysial inflammation, haemorrhage and aponeurosis inflammation.

The addition of adjuvant (50 ug aluminium phosphate and 5 ug MPL) to the inoculations increases the amount of reactogenicity as a side effect of stimulating the immune system. Detoxification of pneumolysin with GMBS allowed the level of degeneration/necrosis to be reduced to that produced by the adjuvant alone which was lower than the level produced by inoculation with native pneumolysin. GMBS detoxified pneumolysin produced a level of haemorrhage lower than that produced by native pneumolysin. Levels of endomysial inflammation were elevated by the adjuvant and this level was still present in the presence of adjuvanted native or GMBS detoxified pneumolysin. Aponeurosis inflammation was however reduced from the level produced by adjuvant alone by native or GMBS detoxified pneumolysin, with the level of aponeurosis being slightly lower where the pneumolysin had been treated with GMBS.

Example 5

Evaluation of Toxicity of GMBS Treated Pneumolysin in Mice

Groups of 20 OF1 mice were challenged intranasally with either native pneumolysin or GMBS-treated pneumolysin and the mice were monitored for the following 9 days.

As shown in FIG. 3, challenge with 2 ug of native pneumolysin led very quickly to the death of all the mice in that group. The pneumolysin produced lesions throughout the respiratory system which led to respiratory difficulties and death. In contrast, the GMBS treated pneumolysin had substantially reduced toxicity with all of the mice inoculated with 2 ug, 5 ug or 10 ug of the GMBS treated pneumolysin surviving the challenge.

Example 6

Protection Studies Using Detoxified Pneumolysin

Groups of 20 OF1 mice were immunised 3 times intramuscularly, on days 0, 14 and 28 with 5 ug of pneumolysin and 50 ug aluminium phosphate and 5 ug MPL as adjuvant. Control mice were immunised with adjuvant alone. The pneumolysin was either untreated or detoxified using the GMBS treatment described above.

On day 42, the mice were given an intranasal, lethal challenge with 2 ug of native pneumolysin. The survival of the mice over the following 9 days was monitored.

Results

The lethal challenge model led to 90% mortality in control mice (FIG. 4). Immunisation with GMBS detoxified pneumolysin produced very good protection with only 5% of mice dying during the following 9 days. This was comparable to protection given after inoculation with native pneumolysin, following which 10% of mice died.

Example 7

Evaluation of Detoxified Pneumolysin in Combination with PhtD in a Mouse Lethal Challenge Model Groups of 200F1 mice were immunised intramuscularly with a) adjuvant alone or b) 1 ug PhtD and adjuvant or c) 1 ug PhtD and 5 ug GMBS detoxified pneumolysin and adjuvant. The adjuvant used was composed of 50 ug aluminium phosphate and 5 ug MPL and immunisations took place on day 0 and day 14. The mice were challenged with an intranasal lethal dose of $5.10^5$ CFU of serotype 2 *S. pneumoniae* strain D39 and survival was monitored over the next 10 days.

Results

As shown in FIG. 5, challenge with strain D39 led to 75% lethality after 10 days in control mice. Immunisation with PhtD alone did not provide significant protection with 70% of mice in this group dying after 10 days (p=0.29). Immunisation with PhtD together with GMBS detoxified pneumolysin gave significantly better protection with lethality being reduced to 50% (p=0.04).

Example 8

Detoxification of Pneimolysin Using Formaldehyde

A stock of purified pneumolysin at a concentration of approximately 0.4 mg/ml was in 25 mM potassium phosphate buffer pH 7.0 wa treated with 50 mM L-lysine and 0.1% formaldehyde (w/v) for 21 days at 4.0° C.

The invention claimed is:

1. A process for purification of a bacterial cytolysin comprising the steps of:
   a) providing a solution containing unpurified soluble aggregated bacterial cytolysin;
   b) adding said solution to a hydrophobic interaction chromatography column, where the column material contains aromatic groups;
   c) binding soluble aggregated bacterial cytolysin contained in the solution to the column material in the presence of an ionic detergent and a salt, where the salt concentration is from 0.6M to 2M; and
   d) eluting bound bacterial cytolysin using a solution containing the detergent and no more than 0.2M salt.

2. The process of claim 1 further comprising the steps of:
   e) removing the detergent from the eluted bacterial cytolysin;
   f) solubilizing the bacterial cytolysin by addition of a denaturant; and
   g) removing the denaturant from the bacterial cytolysin.

3. The process of claim 1 wherein the bacterial cytolysin is pneumococcal pneumolysin.

4. The process of claim 1 wherein the hydrophobic interaction chromatography material is phenyl-sepharose.

5. The process of claim 1 wherein the detergent is an aliphatic detergent.

6. The process of claim 1 wherein the detergent is sodium lauroyl sarcosinate.

7. The process of claim 1 wherein the salt used in step c) and d) is selected from the group consisting of sodium chloride, magnesium chloride, ammonium chloride, sodium sulphate, magnesium sulphate, ammonium sulphate, sodium phosphate, magnesium phosphate, and ammonium phosphate.

8. The process of claim 1 wherein step c) is carried out at a pH of between pH 6-8.

9. The process of claim 2 wherein the denaturant used in step f) is guanidine hydrochloride.

10. The process of claim 1 comprising a further step of detoxifying the eluted bacterial cytolysin by chemical treatment with a crosslinking agent.

11. The process of claim 10 wherein the crosslinking agent is reactive with amine and sulphydryl groups.

12. The process of claim 10 wherein the crosslinking agent is selected from the group consisting of: formaldehyde, glutaraldehyde, N-hydroxysuccinomido esters and GMBS.

13. The process of claim 1 wherein step (d) is carried out at a pH of between pH 6-8.

14. The process of claim 1, where said salt concentration in step (c) is about 1M.

15. The process of claim 1 further comprising, after step (c) and prior to step (d), washing the column with a solution of salt of about 0.5M.

16. The process of claim 1 wherein step (d) is carried out with solutions of decreasing salt gradient, with no more than 0.2M salt.

17. The process of claim 1, where the detergent is present at a concentration of 0.1% to 5% weight/volume.

18. The process of claim 1, where the detergent is present at a concentration of 0.75% to 2% weight/volume.

19. The process of claim 1, where the detergent is present at a concentration of about 1% weight/volume.

20. The process of claim 1, where the detergent is a cationic detergent.

21. The process of claim 1, where the detergent is an anionic detergent.

22. The process of claim 1, where the detergent has no more than one aromatic ring.

23. The process of claim 1, where the detergent has no aromatic rings.

24. The process of claim 1 where said solution containing unpurified soluble aggregated bacterial cytolysin is provided by a process comprising:
   (a) disrupting cells expressing bacterial cytolysin to provide a solution containing bacterial cytolysin;
   (b) adding a detergent to said solution; and
   (c) centrifuging said solution to remove insoluble cellular debris.

25. The process of claim 24 where said centrifugation is at 30,000 rpm for 20 minutes.

26. The process of claim 1 where said solution containing unpurified soluble aggregated bacterial cytolysin is provided by a process comprising:
   (a) disrupting cells expressing bacterial cytolysin to provide a solution containing bacterial cytolysin;
   (b) adding a detergent to said solution, where said detergent is the same detergent as in steps (c) and (d) of claim 1, and
   (c) centrifuging said solution to remove insoluble cellular debris.

27. The process of claim 24 where said detergent is 1% sodium lauroyl sarcosinate.

28. The process of claim 24 further comprising, prior to the addition of detergent in step (b), adjusting the pH of said solution containing unpurified soluble aggregated bacterial cytolysin to a pH of less than 7.5 for a period of at least eight hours to form aggregates of bacterial cytolysin.

29. The process of claim 1 wherein the hydrophobic interaction chromatography material contains phenyl groups.

30. A process for purification of *Streptococcus pneumoniae* pneumolysin, comprising the steps of:
   a) providing a solution containing unpurified soluble aggregated *S. pneumoniae* pneumolysin;
   b) adding said solution to a hydrophobic interaction chromatography column, where the column material contains aromatic groups;
   c) binding soluble aggregated *Streptococcus pneumoniae* pneumolysin contained in the solution to the column material in the presence of sodium lauroyl sarcosinate at a concentration of about 1% weight/volume and a salt at a concentration of from 0.6M to 2M; and
   d) eluting bound *Streptococcus pneumoniae* pneumolysin using a solution containing sodium lauroyl sarcosinate at a concentration of about 1% weight/volume and no more than 0.2M salt.

31. The process of claim 30 further comprising the steps of:
   (e) removing the detergent from the eluted *S. pneumoniae* pneumolysin;
   (f) solubilizing the eluted *S. pneumoniae* pneumolysin by addition of a denaturant; and
   (g) removing the denaturant from the eluted *S. pneumoniae* pneumolysin.

32. The process of claim 31 where said denaturant is guanidine hydrochloride.

33. The process of claim 30 wherein the hydrophobic interaction chromatography material is phenyl-sepharose.

34. The process of claim 30 wherein the salt used in step (c) and (d) is selected from the group consisting of sodium chloride, magnesium chloride, ammonium chloride, sodium sulphate, magnesium sulphate, ammonium sulphate, sodium phosphate, magnesium phosphate, and ammonium phosphate.

35. The process of claim 30 wherein steps (c) and (d) are carried out at a pH of between pH 6-8.

36. The process of claim 30, where said salt concentration in step (c) is about 1M.

37. The process of claim 30 further comprising, after step (c) and prior to step (d), washing the column with a solution of salt of about 0.5M.

38. The process of claim 30 wherein step (d) is carried out with solutions of decreasing salt gradient, with no more than 0.2M salt.

39. The process of claim 30 wherein said *Streptococcus pneumoniae* pneumolysin is a point mutated *S. pneumoniae* pneumolysin.

40. A process for the purification of *Streptococcus pneumoniae* pneumolysin comprising the steps of:
   a) providing a solution containing unpurified soluble aggregated *S. pneumoniae* pneumolysin;
   b) adding said solution to a phenyl-sepharose hydrophobic interaction chromatography column;
   c) binding soluble aggregated *S. pneumoniae* pneumolysin contained in the extract to the column material in the presence of sodium lauroyl sarcosinate at a concentration of about 1% weight/volume and a salt at a concentration from 0.6M to 2M; and
   d) eluting bound *S. pneumoniae* pneumolysin using a solution containing sodium lauroyl sarcosinate at a concentration of about 1% weight/volume and no more than 0.2 M salt.

41. The process of claim 40 wherein the salt used in step (c) and (d) is selected from the group consisting of sodium chloride, magnesium chloride, ammonium chloride, sodium sulphate, magnesium sulphate, ammonium sulphate, sodium phosphate, magnesium phosphate, and ammonium phosphate.

42. The process of claim 40 wherein steps (c) and (d) are carried out at a pH of between pH 6-8.

43. The process of claim 40, where said salt concentration in step (c) is about 1M.

44. The process of claim 40 further comprising, after step (c) and prior to step (d), washing the column with a solution of salt of about 0.5M.

45. The process of claim 40 wherein step (d) is carried out with solutions of decreasing salt gradient, with no more than 0.2M salt.

46. The process of claim 40 comprising a further step of detoxifying the eluted *S. pneumoniae* pneumolysin by chemical treatment with formaldehyde.

47. The process of claim 40 wherein said *Streptococcus pneumoniae* pneumolysin is a point mutated *S. pneumoniae* pneumolysin.

48. The process of claim 40 further comprising the steps of:
   (e) removing the detergent from the eluted *S. pneumoniae* pneumolysin;
   (f) solubilizing the eluted *S. pneumoniae* pneumolysin by addition of a denaturant; and
   (g) removing the denaturant from the eluted *S. pneumoniae* pneumolysin.

49. The process of claim 48 where said denaturant is guanidine hydrochloride.

50. A process for the purification of *Streptococcus pneumoniae* pneumolysin comprising the steps of:
   a) providing a solution containing unpurified soluble aggregated *S. pneumoniae* pneumolysin;

b) adding said solution to a phenyl-sepharose hydrophobic interaction chromatography column;

c) binding soluble aggregated *S. pneumoniae* pneumolysin contained in the extract to the column material in the presence of sodium lauroyl sarcosinate at a concentration of about 1% weight/volume and a salt at a concentration of about 1M, at a pH of between pH 6-8; and d) eluting bound *S. pneumoniae* pneumolysin using a solution containing sodium lauroyl sarcosinate at a concentration of about 1% weight/volume and no more than 0.2 M salt, at a pH of between pH 6-8.

51. The process of claim 50 wherein the salt used in step (c) and (d) is selected from the group consisting of sodium chloride, magnesium chloride, ammonium chloride, sodium sulphate, magnesium sulphate, ammonium sulphate, sodium phosphate, magnesium phosphate, and ammonium phosphate.

52. The process of claim 50 further comprising, after step (c) and prior to step (d), washing the column with a solution of salt of about 0.5M.

53. The process of claim 50 wherein step (d) is carried out with solutions of decreasing salt gradient, with no more than 0.2M salt.

54. The process of claim 50 comprising a further step of detoxifying the eluted *S. pneumoniae* pneumolysin by chemical treatment with formaldehyde.

55. The process of claim 50 wherein said *Streptococcus pneumoniae* pneumolysin is a point mutated *S. pneumonia* pneumolysin.

56. The process of claim 50 further comprising the steps of:

(e) removing the detergent from the eluted *S. pneumoniae* pneumolysin;

(f) solubilizing the eluted *S. pneumoniae* pneumolysin by addition of a denaturant; and (g) removing the denaturant from the eluted *S. pneumoniae* pneumolysin.

57. The process of claim 56 where said denaturant is guanidine hydrochloride.

* * * * *